US00PP10588P

United States Patent [19]

Wagner

[11] Patent Number: Plant 10,588

[45] Date of Patent: Sep. 1, 1998

[54] BEGONIA PLANT NAMED 'SOLENIA ROT'

[75] Inventor: Konrad Wagner, Mïden, Germany

[73] Assignee: Gebr. Man C.V., Aalsmeer, Netherlands

[21] Appl. No.: 853,794

[22] Filed: May 9, 1997

[51] Int. Cl.[6] ..... A01H 5/00

[52] U.S. Cl. ..... Plt./87.18

[58] Field of Search ..... Plt./87.18

*Primary Examiner*—James R. Feyrer

*Attorney, Agent, or Firm*—C. A. Whealy

[57] ABSTRACT

A distinct cultivar of Begonia plant named 'Solenia Rot', characterized by its numerous and attractive red fully double flowers that are about 6 cm in diameter; uniform plant habit; dark foliage color; resistance to Powdery Mildew under commercial greenhouse conditions; and outstanding weather tolerance and garden performance.

1 Drawing Sheet

The present invention relates to a new and distinct cultivar of Begonia plant, botanically known as a Begonia elatior hybrid, commercially known as Elatior Begonia, and referred to by the cultivar name 'Solenia Rot'.

The new cultivar is a product of a planned breeding program conducted by the inventor in Hann. Münden, Germany. The new cultivar originated from a cross by the inventor between an unidentified Begonia Tuber-hybrid as the female or seed parent and the species *Begonia socotrana* as the male or pollen parent. The cultivar 'Solenia Rot' was discovered and selected by the inventor as a plant within the progeny of the stated cross in a controlled environment in Hann. Münden, Germany, in 1994. This selection was selected based on its floriferous and garden performance.

Asexual reproduction of the new cultivar by terminal cuttings taken in a controlled environment in Hann. M ünden, Germany, has shown that the unique features of this new Begonia are stable and reproduced true to type in successive generations.

The cultivar 'Solenia Rot' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Solenia Rot'. These characteristics in combination distinguish 'Solenia Rot' as a new and distinct cultivar:

1. Numerous attractive red fully double flowers that are about 6 cm in diameter.
2. Uniform plant habit.
3. Dark foliage color.
4. Resistance to Powdery Mildew under commercial greenhouse conditions.
5. Outstanding weather-tolerance and garden performance.

The accompanying colored photograph illustrates the overall appearance of the new cultivar, showing the colors as true as it is reasonably possible to obtain in colored reproductions of this type. The photograph comprises a top perspective view of a typical flowering plant of 'Solenia Rot'. Flower and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Aalsmeer, The Netherlands, that were flowered in November under commercial practice in a glass-covered greenhouse. Average day temperatures were 20° C and average night temperatures were 18° C. Assimilation lights provided a maximum light level of 18,000 lux. Measurements and numerical values represent averages for six typical flowering plants.

Botanical Classification: Begonia elatior hybrid cultivar Solenia Rot.

Commercial Classification: Elatior Begonia.

Parentage:

*Seed or female parent.*—Unidentified Begonia Tuber-hybrid.

*Pollen or male parent.*—Species *Begonia socotrana.*

Propagation:

*Type.*—Terminal cuttings.

*Time to rooting.*—About 14 days with soil temperatures of 23° C.

*Rooting habit.*—Fine, fibrous and well-branched.

Plant Description:

*Plant form.*—Upright and rounded potted plant, uniform, freely branching with good stem and stem base strength. Flowers are fully double and abundant. Plants flower continuously.

*Growth habit.*—Moderate growth rate and moderately vigorous. Appropriate for 13-cm containers. Under optimal environmental and cultural conditions, usually 10 weeks are required to produce proportional 13-cm potted plants from terminal cuttings. Vegetative shoots are formed at basal nodes and flowering shoots are formed at upper nodes.

*Plant height.*—About 30 cm.

*Leaves.*—Arrangement: Simple, alternate. Size: Length: About 15 cm. Width: About 12 cm. Shape: Asymmetrically ovate/cordate. Apex: Acute. Base: Cordate, overlapping. Margin: Lacerate/doubly serrate. Texture: Smooth and leathery. Color: Young foliage: Upper surface: 147A with red tones. Lower surface: 59A. Mature foliage: Upper surface: 147A with red tones. Lower surface: 59A with green at center. Venation: Upper surface: Light green. Lower surface: Light green. Durability: Very durable, weather-tolerant.

Flower Description:

*Flowering habit.*—Fully double and large flowers arranged in compound cymes. Many cymes in flower simultaneously. Flowering continuous. Flowers persistent.

*Natural flowering season.*—Plants will flower year around regardless of daylength, however plants will flower earlier and more abundantly if daylength is 12 hours or less. Usually plants start flowering after 6 weeks of start of short day/long night treatments.

*Flowers.*—Shape: Oval. Diameter: About 6 cm. Depth: About 2 cm.

*Petals.*—Arrangement: Rosette. Shape: Rounded with undulating margin. Quantity per flower: Usually about 33 per flower. Color: When opening: 41A to 40A. Fully opened: Upper surface: 41A. Lower surface: 41B. Texture: Smooth, velvety, glabrous.

*Sepals.*—Arrangement: Two, opposite. Shape: Oval. Color: 144A with red margin.

*Reproductive organs.*—Stamens: None. Pistils: None.

Disease Resistance: Plants of the cultivar Solenia Rot are resistant to Powdery Mildew under greenhouse conditions.

Seed Production: Seed production has not been observed as reproductive organs are not formed.

It is claimed:

1. A new and distinct cultivar of Begonia plant named 'Solenia Rot', as illustrated and described.

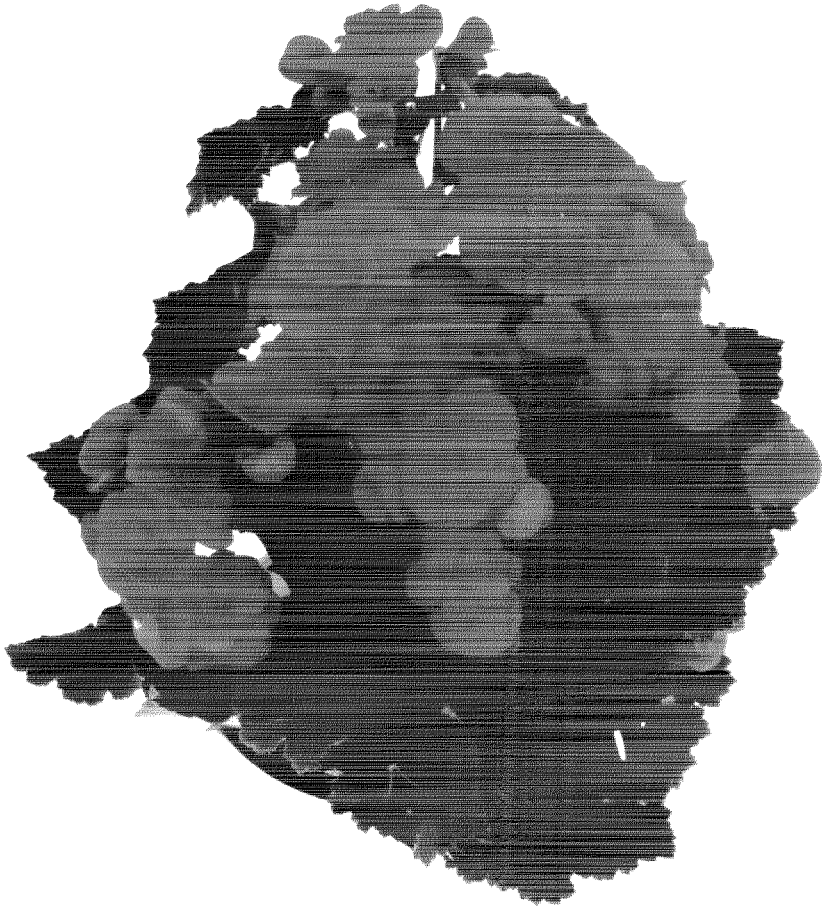

* * * * *